United States Patent
Regensburger et al.

(10) Patent No.: US 11,812,919 B2
(45) Date of Patent: Nov. 14, 2023

(54) PRESSURE CONTROL SYSTEM FOR PROVIDING A PRESSURE TO BE APPLIED TO A PATIENT DURING A PRE-INTERVENTIONAL IMAGING PROCESS WITH AN IMAGING SYSTEM

(71) Applicant: Siemens Healthcare GmbH, Erlangen (DE)

(72) Inventors: Alois Regensburger, Poxdorf (DE); Gregor Niewalda, Buckenhof (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/746,951

(22) Filed: May 17, 2022

(65) Prior Publication Data

US 2022/0370025 A1 Nov. 24, 2022

(30) Foreign Application Priority Data

May 19, 2021 (DE) ...................... 10 2021 205 077.8

(51) Int. Cl.
*A61B 6/00* (2006.01)
*A61B 5/00* (2006.01)
*A61B 6/04* (2006.01)

(52) U.S. Cl.
CPC .......... *A61B 6/4441* (2013.01); *A61B 5/6843* (2013.01); *A61B 6/4452* (2013.01); *A61B 6/4458* (2013.01); *A61B 6/0407* (2013.01)

(58) Field of Classification Search
CPC ... A61B 6/4441; A61B 5/6843; A61B 6/4452; A61B 6/4458; A61B 6/0407;
(Continued)

(56) References Cited

U.S. PATENT DOCUMENTS

2006/0293598 A1 12/2006 Fraser
2007/0213617 A1 9/2007 Berman et al.
(Continued)

FOREIGN PATENT DOCUMENTS

CN 101902970 A 12/2010
CN 102283650 A 12/2011
(Continued)

OTHER PUBLICATIONS

Decision to Grant German Application No. 10 2021 205 077.8 decision dated Nov. 9, 2022, with English Translation.
(Continued)

*Primary Examiner* — Courtney D Thomas
(74) *Attorney, Agent, or Firm* — Lempia Summerfield Katz LLC

(57) ABSTRACT

A pressure control system for providing an interventional pressure to be applied to a defined area of a patient during a pre-interventional imaging process with an imaging system is provided. Therein, the interventional pressure corresponds to an interventional pressure applied to the defined area of the patient during an intervention via a medical technology device. The pressure control system includes a pressure plate, a force module, and a positioning apparatus. Therein, the force module is configured to apply a force on the pressure plate. Therein, the force on the pressure plate generates the interventional pressure. Therein, the positioning apparatus is configured to position the pressure plate and the force module relative to the patient.

15 Claims, 6 Drawing Sheets

(58) Field of Classification Search
CPC ......... A61B 6/032; A61B 6/037; A61B 8/085;
A61B 6/00; A61B 5/055; A61B 5/70;
A61B 5/702; A61B 6/502; A61B 34/30;
A61B 34/70; A61B 2034/305; A61N 7/00
See application file for complete search history.

(56) References Cited

U.S. PATENT DOCUMENTS

| | | |
|---|---|---|
| 2010/0241005 A1 | 9/2010 | Darlington et al. |
| 2010/0292572 A1 | 11/2010 | Hope et al. |
| 2012/0029337 A1 | 2/2012 | Aoyagi |
| 2013/0072830 A1* | 3/2013 | Illindala ................ A61H 11/00 601/41 |
| 2014/0316269 A1 | 10/2014 | Zhang et al. |
| 2015/0071400 A1 | 3/2015 | Popescu |
| 2015/0297177 A1 | 10/2015 | Boctor et al. |
| 2017/0120080 A1 | 5/2017 | Phillips et al. |
| 2020/0164231 A1 | 5/2020 | Cannata et al. |

FOREIGN PATENT DOCUMENTS

| | | |
|---|---|---|
| CN | 103025381 A | 4/2013 |
| CN | 104936517 A | 9/2015 |

OTHER PUBLICATIONS

German Office Action for German Application No. 10 2020 205 077.8 dated Feb. 2, 2022, with English Translation.

\* cited by examiner

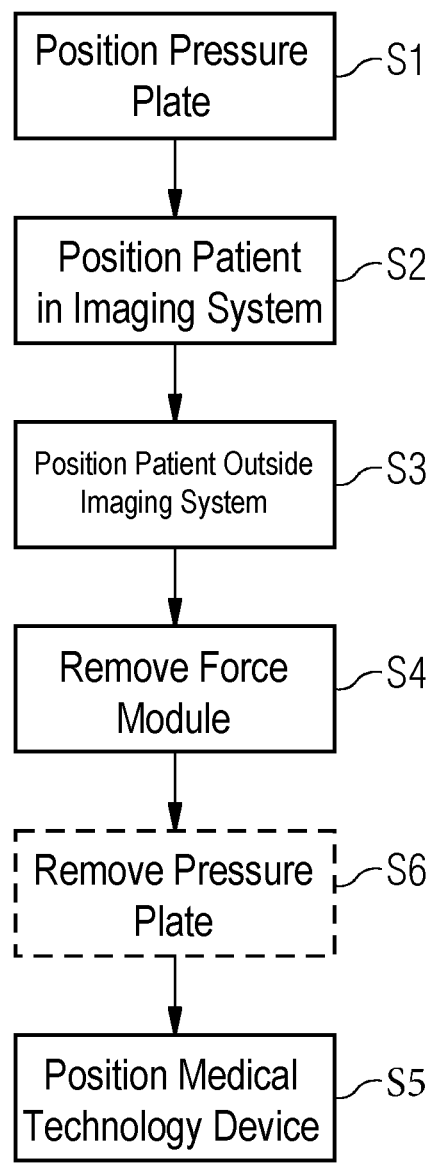

PRESSURE CONTROL SYSTEM FOR PROVIDING A PRESSURE TO BE APPLIED TO A PATIENT DURING A PRE-INTERVENTIONAL IMAGING PROCESS WITH AN IMAGING SYSTEM

This application claims the benefit of German Patent Application No. DE 10 2021 205 077.8, filed on May 19, 2021, which is hereby incorporated by reference in its entirety.

BACKGROUND

The present embodiments relate to a pressure control system for providing an interventional pressure to be applied to a defined area of a patient during a pre-interventional imaging process with an imaging system. The present embodiments further relate to a method for providing an interventional pressure to be applied to a defined area of a patient during a pre-interventional imaging process with an imaging system, and a system that is configured to carry out the method.

It is known that an interventional pressure is applied to a patient via a medical technology device during an intervention. The interventional pressure may therein lead to a deformation of an intervention region. The intervention region therein defines the region of the patient in which the intervention is or is to be carried out with the medical technology device. For example, the medical technology device may be positioned on an abdominal cavity of the patient. Via the interventional pressure that the medical technology device exerts on the abdominal cavity, the soft tissue and/or at least an organ in the abdominal cavity of the patient may be deformed and/or distorted.

An intervention of this type may be, for example, a treatment with focused ultrasound. For example, such an intervention may be a histotripsy and/or an intervention based on high energy focused ultrasound (HIFU). The medical technology device for histotripsy includes an ultrasonic treatment transducer and an ultrasonic imaging transducer and a coupling medium. Using the coupling medium (e.g., a water bath), the ultrasonic waves may be introduced into the body of the patient. The ultrasonic waves emitted by the ultrasonic imaging transducer therein serve for the imaging. The ultrasonic waves emitted by the ultrasonic treatment transducer therein serve for the histotripsy treatment. In order to provide an efficient coupling of the ultrasonic waves into the body of the patient, it is necessary to apply an interventional pressure to the patient with the medical technology device. For this purpose, the medical technology device is positioned on the site to be treated and/or on the intervention region of the patient.

It is known, for planning the intervention, to carry out a pre-interventional imaging of at least the intervention region of the patient with the imaging system. Therein, a medical image of at least the intervention region is captured. The imaging system may therein be, for example, an X-ray system, a mammography system, a C-arm system, a computed tomography (CT) system, a magnetic resonance tomography (MRT) system, a positron emission tomography (PET) system, or a single photon emission computed tomography (SPECT) system. For example, the pre-interventional imaging may be a time-resolved imaging (e.g., a four-dimensional imaging). For example, in the four-dimensional imaging, it may be required to acquire a time-resolved three-dimensional medical image with a CT system. Such a medical image is also designated a 4DCT recording. A 4DCT recording may map a temporal sequence of an organ movement and/or an organ deformation. Typically, a space in the imaging system is not sufficient to position the medical technology device on the patient during the pre-interventional imaging. In addition, the medical technology device typically causes image artifacts in the medical image. The deformation caused by the medical technology device therefore typically does not exist during the pre-interventional imaging. This hinders, for example, a planning of the intervention based on a medical image generated and/or captured in this way.

It is known to carry out an algorithmic deformation correction of the medical image generated during the pre-interventional imaging. However, this is fault-prone, for example, for organs that move, for example, due to the breathing or the heartbeat of the patient.

For this reason, errors due to the deformation during the imaging-based planning of the intervention are often accepted, or no pre-interventional imaging is carried out. In this way, a treatment risk for the patient is increased, and the intervention cannot be carried out with the precision that is possible.

It is known from radiation therapy that the patient is already positioned for pre-interventional imaging as for the performance of radiation therapy. However, during radiation therapy, no interventional pressure may be applied to the patient via a medical technology device that has an influence on the pre-interventional imaging.

It is known from laparoscopy to carry out the pre-interventional imaging only after induction of a pneumoperitoneum. This would correspond to a pre-interventional imaging with a positioned medical technology device. However, due to the space requirement of the medical technology device in the imaging system and possible image artifacts caused by the medical technology device, this is not possible.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a system that creates a deformation during the pre-interventional imaging that is comparable with a deformation of an intervention region during the intervention is provided.

In one embodiment, a pressure control system for providing an interventional pressure to be applied to a defined area of a patient during a pre-interventional imaging with an imaging system is provided. In another embodiment, a method for providing an interventional pressure to be applied to a defined area of a patient during a pre-interventional imaging process with an imaging system is provided. In yet another embodiment, a system is provided. Developments are disclosed in the following description.

Features, advantages, or alternative embodiments mentioned herein are also transferable similarly to the other subject matter and vice versa. In other words, the object-related subject matter (e.g., directed to an apparatus) may also be further developed with the features disclosed in relation to a method. The corresponding functional features of the method are thereby embodied by corresponding physical modules.

The present embodiments relate to a pressure control system for providing an interventional pressure to be applied to a defined area of a patient during a pre-interventional imaging process with an imaging system. Therein, the interventional pressure corresponds to an interventional pressure applied to the defined area of the patient during an intervention via a medical technology device. The pressure control system includes a pressure plate, a force module, and a positioning apparatus. The force module is therein configured to apply a force to the pressure plate. Therein, the force generates the interventional pressure upon the pressure plate. Therein, the positioning apparatus is configured to position the pressure plate and the force module relative to the patient.

During the pre-interventional imaging, in advance of the intervention, a medical image of at least one intervention region of the patient is captured with the imaging system. The imaging system may therein be, for example, an X-ray system, a mammography system, a C-arm system, a computed tomography (CT) system, a magnetic resonance tomography (MRT) system, a positron emission tomography (PET) system, or a single photon emission computed tomography (SPECT) system. The medical image may therein be a two-dimensional, a three-dimensional, or a four-dimensional medical image. A four-dimensional medical image is therein a time-resolved three-dimensional medical image. In other words, a four-dimensional medical image includes a plurality of three-dimensional medical images that are captured at defined temporal spacings after one another with the imaging system. A four-dimensional medical image may therein be, for example, a 4DCT recording as described above. Therein, the patient is a human. Alternatively, the patient may be an animal or an object. The intervention region of the patient imaged in the medical image is, for example, the region of the patient in which the intervention is to be carried out with the medical technology device. The intervention region may therein include, for example, an abdomen and/or an abdominal cavity of the patient. Alternatively or additionally, the intervention region may include a thorax and/or an arm and/or a leg and/or a head and/or a neck of the patient. The medical image therein maps at least the intervention region. Alternatively or additionally, the medical image may also map regions of the patient adjoining the intervention region. Alternatively, the medical image may map the entire patient.

The interventional pressure is applied to the patient during the intervention by the medical technology device. The interventional pressure is therein defined by a force on the defined area. The defined area therein includes an area of the intervention region on the patient. In other words, the interventional pressure defines the force applied to the area of the intervention region. The interventional pressure may be determined as the quotient of the force applied and the area. In the following description, the shape and the size and/or the extent of the defined area (e.g., the area of the intervention region) is specific for the interventional pressure. The force applied may therein depend, for example, upon a weight force of the medical technology device. For example, the force applied may correspond to the weight force of the medical technology device.

The force may therein define a force field and/or a force distribution on the defined area. In other words, the force on the defined area may define an inhomogeneous force field. In the inhomogeneous force field, force vectors may act with different amounts and/or different directions on the defined area. Therein, the total force (e.g., a vector integral over all the force vectors of the force field over the defined area during the pre-interventional imaging) may be equal to the overall force via the medical technology device during the intervention. Alternatively, just a portion of the force field on a section of the defined area during the intervention and during the pre-interventional imaging may be identical. Further, for example, a first moment or a second moment of the force distribution during the pre-interventional imaging and the intervention may be matched, or only a force effect in a direction of action may be identical. Further, only the integral over a projection of the force vectors along a direction relative to the defined area may be identical. This projection direction may be, for example, the surface normal to the defined area (e.g., to a local patient surface) or the direction of gravity.

The medical technology device may be configured, for example, to carry out the intervention. The intervention may therein be, for example, an intervention by focused ultrasound (e.g., a histotripsy or an HIFU). The medical technology device for carrying out the histotripsy, the histotripsy system, includes an ultrasonic treatment transducer and an ultrasonic imaging transducer and a coupling medium. The coupling medium may therein be configured as a water bath. The medical technology device configured in this way is positioned relative to the patient such that the medical technology device applies the interventional pressure to the patient in order to provide coupling of the ultrasonic waves into the intervention region of the patient. Typically, the medical technology device configured in this way is positioned on the lying patient. For example, the medical technology device configured in this way is firmly fastened to the positioning apparatus on the patient. Alternatively, the positioning apparatus may include a holding apparatus for positioning the medical technology device relative to the patient.

The pressure plate is configured to be positioned on the patient. The pressure plate may therein be adapted to an anatomy of the patient. For example, the pressure plate may grasp a typical body shape of the patient in the intervention region. The pressure plate is therein significantly less extensive in one spatial direction than in the other two spatial directions. This spatial direction is oriented, after the positioning of the pressure plate, perpendicularly to the surface of the patient. This spatial direction is designated below the "thickness" of the pressure plate.

The pressure plate may be configured, for example, as a pressure cushion and/or pressure mat.

Alternatively, the pressure plate consists, for example, at least partially of a non-deformable material. For example, the pressure plate is not deformable with a small force application. In other words, the pressure plate retains its shape during the application of a force to the pressure plate. Therein, the thickness may be variable in embodiments, dependent upon the interventional pressure. In other words, the pressure plate may include a portion that is non-deformable or only deformable with difficulty, and/or a pressure mat. Therein, the pressure cushion and/or pressure mat may be arranged so that, in the positioned state, the pressure cushion and/or pressure mat is arranged between the defined surface and the part that is non-deformable or only with difficulty.

The pressure plate includes a contact area. In the positioned state, the pressure plate lies on the patient with the contact area. For example, the pressure plate lies with the contact area on the intervention region and/or is in contact therewith. For example, the contact area represents the defined area. In some embodiments, the contact area may be made of a material that adapts to a body shape of the patient in the intervention region. For example, the contact area may include a gel pad.

The force module is configured to apply the force to the pressure plate, which causes the interventional pressure. The force module may apply the force, for example, in the form of a weight force of the force module onto the pressure plate. Alternatively or additionally, the force module may be configured to apply the force in the form of a pressing force onto the pressure plate.

The force module may therein be positioned on the pressure plate. The force module may, for example, be screw-fastened, glued, soldered, welded, cast, and/or riveted onto the pressure plate. Alternatively, in some embodiments, it is possible for the force module to be releasably connected and/or coupled to the pressure plate. For example, it is possible for the force module to be coupled to the pressure plate by a clip apparatus, a clamping apparatus, or a tensioning apparatus.

The positioning apparatus is configured for positioning the pressure plate and the force module relative to the patient. For example, the pressure plate and the force module are positioned by the positioning apparatus on the intervention region of the patient.

The positioning apparatus may include, for example, at least one fixing belt. The at least one fixing belt is configured to strap the pressure plate and the force module to the patient.

Alternatively or additionally, the positioning apparatus may include a holding apparatus (e.g., a stand). Therein, the pressure plate and the force module may be arranged (e.g., fastened) on the holding apparatus. The pressure plate and the force module may be positioned relative to the patient by the holding apparatus.

The pressure plate, the force module, and the positioning apparatus are configured, for example, so that during the pre-interventional imaging, the pressure plate, the force module, and the positioning apparatus may be positioned at, on, or beside the patient. In other words, a space requirement of the pressure plate, the force module, and the positioning apparatus are so small that a capture of the medical image with the imaging system with the pressure plate and the force module in position is unproblematic.

Alternatively, via the pressure control system, a pressure that corresponds to the interventional pressure by the medical technology device may be applied to the patient. The pressure control system may therein be configured so small and/or space-saving that it is unproblematic during the pre-interventional imaging. In other words, the pressure control system may be positioned on the patient during the pre-interventional imaging. In order to apply the interventional pressure, a force is to act upon the same area as via the medical technology device. In other words, both the force via the medical technology device and also the force via the force module act upon the defined area. Therein, the force is to be equal to the force via the medical technology device.

According to one aspect of the present embodiments, the weight force applied via the force module on the pressure plate corresponds to the weight force applied via the medical technology device.

The weight force of the force module is applied via the weight of the force module. The weight force of the force module on the earth corresponds to the product of the weight of the force module in kilograms and the gravitational acceleration (ca. 9.81 m/s$^2$).

Similarly, the weight force of the medical technology device corresponds to the product of the weight of the medical technology device in kilograms and the gravitational acceleration.

The weight force of the medical technology device and/or of the force module may define, for example, a weight distribution. In other words, the weight force may describe an anisotropic force field that acts upon the defined area. In other words, the weight force may be anisotropically distributed over the defined area.

The weight force of the force module therein acts upon the pressure plate. For example, the weight force of the force module acts upon the pressure plate during the pre-interventional imaging.

The weight force of the medical technology device may also act upon the pressure plate. For example, the weight force of the medical technology device may act upon the pressure plate during the intervention.

Alternatively, the weight force of the medical technology device may act directly upon the patient. For example, the weight force of the medical technology device may act directly upon the patient during the intervention. Therein, the weight force of the pressure plate is negligibly small if the weight force of the force module corresponds to the weight force of the medical technology device. Alternatively, the sum of the weight forces via the pressure plate and the force module correspond to the weight force of the medical technology device.

For example, the patient may be positioned lying if the force for exerting the interventional pressure corresponds to the weight force of the force module and/or of the medical technology device.

The force applied to the pressure plate may be generated by the force module via the weight of the force module. For this purpose, the weight of the force module should correspond to the weight of the medical technology device. The force module may therein be realized smaller than the medical technology device in order to be capable of being positioned in the imaging system during the pre-interventional imaging despite a restricted space requirement.

According to a further aspect of the present embodiments, the pressure plate includes a contact area with the patient. Therein, an extent and shape of the contact area of the pressure plate corresponds to an extent and shape of an area with which the medical technology device lies on the patient during the intervention.

For example, the contact area and the area with which the medical technology device lies on the patient correspond to the defined area on which the interventional pressure is applied. For example, therefore, the contact area and the area with which the medical technology device lies on the patient correspond to the area of the intervention region on the patient.

The pressure plate is therein configured, for example, such that the pressure plate includes an area that corresponds to the area of the intervention region. The contact area therefore corresponds to the area of the intervention region. The area of the intervention region is arranged on the surface of the patient. In other words, the contact area of the pressure plate corresponds to the area with which the medical technology device is in contact with the patient and/or lies on the patient. The contact area may be configured as described above.

The area with which the medical technology device lies on, and/or is in contact with, the patient may be included by the medical technology device. Alternatively, this area may also correspond to the contact area of the pressure plate if the medical technology device is coupled to the pressure plate for carrying out the intervention.

The area on which the force acts during the generation of the interventional pressure during the pre-interventional imaging and during the intervention may be comparable or identical. In this way, a comparable deformation of the patient and/or the organs and/or the soft tissue of the patient may be provided by the interventional pressure.

According to a further aspect of the present embodiments, the pressure plate and the medical technology device are capable of being positioned identically relative to the patient with the positioning apparatus based on a marking.

For example, the pressure plate is therein removed from the patient before the positioning of the medical technology device. Therein, the medical technology device is positioned such that the area that is directly in contact with the patient covers the same area on the patient as previously the pressure plate covered (e.g., the contact area of the pressure plate). For example, the medical technology device and the pressure plate are arranged and/or positioned on the defined area.

The marking may be, for example, a tattoo or a marking with a pen and/or a drawing on the skin of the patient. Alternatively, the marking may be projected with an illumination device (e.g., a laser) on the surface of the patient.

The marking may specify, for example, the outlines of the pressure plate and/or the medical technology device on the patient. Alternatively, the marking may specify at least one prominent point such as a corner or an edge of the pressure plate and/or the medical technology device on the patient.

Therein, the pressure plate and/or the medical technology device may be positioned relative to the patient with the positioning apparatus. For example, the positioning apparatus may be configured so as to fix the pressure plate and/or the medical technology device relative to the patient.

Based on the marking, a reproducible positioning of the pressure plate and of the medical technology device is possible. An identical positioning of the pressure plate and the medical technology device relative to the patient provide a comparable interventional pressure via the force module and via the medical technology device.

According to a further aspect of the present embodiments, the pressure plate includes a coupling unit. Therein, either the force module or the medical technology device may be releasably coupled to the pressure plate.

For example, the coupling unit is configured such that either the force module or the medical technology device may be coupled to the pressure plate on the side opposite to the contact area of the pressure plate. For example, therein, either the force module or the medical technology device may be coupled to the pressure plate such that a slippage and/or displacement of the force module and/or the medical technology device relative to the pressure plate may be prevented.

Therein, either the force module or the medical technology device may be coupled to the pressure plate (e.g., by a clip apparatus, a clamping apparatus, a tensioning apparatus, or a plug-in apparatus). The coupling unit for coupling the force module and the medical technology device may therein be the same. Alternatively, the coupling units for coupling the force module and the medical technology device may be different. For example, the pressure plate may then include two different coupling units.

In this way, the pressure plate may remain identically positioned during the pre-interventional imaging and during the intervention. Therefore, only a single positioning of the pressure plate relative to the patient is to be provided. In this way, the force module and the medical technology device are positioned the same relative to the patient, and therefore, the interventional pressure is constant.

According to a further aspect of the present embodiments, the pressure plate consists of a material that is compatible with the pre-interventional imaging.

In this regard, "compatible" provides that the pressure plate generates or brings about no, or only slight, artifacts in the medical image captured with the pre-interventional imaging. In other words, the pressure plate is made of a material that has little or no influence on the pre-interventional imaging.

For example, the pressure plate may be made of a plastics material or carbon.

If the pre-interventional imaging is a magnetic resonance tomography, the material of the pressure plate is a non-ferromagnetic material. In an optional embodiment of the invention, the pressure plate may include at least one coil for a magnetic resonance imaging. In this way, an image quality in the region of the treatment region may additionally be improved.

If the pre-interventional imaging is based upon X-ray radiation, the pressure plate consists of a material that does not, or only weakly, absorbs and/or attenuates, X-ray radiation of the specific energy.

In some embodiments, the force module is also made of a material compatible with the pre-interventional imaging.

A pressure plate configured in this way influences the quality of the medical image captured during the pre-interventional imaging not at all or only slightly. For example, it may be provided in this way that the medical image is suitable despite the positioned pressure plate during capturing of the medical image for a planning of the intervention. For example, it may be prevented in this way that artifacts in the medical device via the pressure plate make an image-based planning more difficult and/or impossible.

According to a further aspect of the present embodiments, the pressure control system includes a force sensor. Therein, the force sensor is configured to capture a force acting upon the pressure plate.

For example, the force sensor is therein arranged such that a force acting upon the contact area and/or on the area arranged opposite to the contact area may be captured. For example, how large the force acting upon the pressure plate is may be captured. Therein, for example, the force components acting perpendicularly to the contact area and/or the area perpendicular to the contact area are captured.

In this way, it may be determined what force acts upon the pressure plate. Based on the captured force and the area of the pressure plate, the pressure applied by the pressure control system on the patient may be determined. In this way, it may be checked whether the pressure applied by the pressure control system corresponds to the interventional pressure.

According to a further aspect of the present embodiments, the positioning apparatus includes a holding apparatus. Therein, the pressure plate is arranged on the holding apparatus. Therein, the holding apparatus is configured to position the pressure plate relative to the patient.

The holding apparatus may therein be, for example, a stand or a robot arm. The holding apparatus may be configured such that the holding apparatus partially compensates for a force acting upon the pressure plate. In this way, the entire force acting upon the pressure plate cannot also act upon the patient.

The holding apparatus may be configured such that a position of the holding apparatus relative to the patient always remains constant. Therein, either the force module or the medical technology device may be coupled to the pressure plate. Regardless of whether the force module or the medical technology device is coupled to the pressure plate, the holding apparatus holds the position of the pressure plate constant relative to the patient.

The pressure plate may be positioned on the patient with a pre-defined pressure using the holding apparatus. This pre-defined pressure may therein correspond, for example, to the interventional pressure, since the pre-defined pressure may remain constant regardless of whether the pressure plate is coupled to the medical technology device or to the force module. For this purpose, the pressure plate may be positioned in a patient-specific manner by the holding apparatus. In other words, for this purpose, the pressure plate may be positioned with the holding apparatus, for example, dependent upon a size of the patient.

For example, in this manner, the force module may be integrated into the pressure plate. In other words, the force module may be realized via the holding apparatus.

Using the holding apparatus, a constant pressure of the pressure plate on the patient may be provided. For example, the force module or the medical technology device may be coupled to the pressure plate without the pressure on the patient being changed.

According to a further aspect of the present embodiments, the holding apparatus is arranged on a patient table.

For example, the patient table and/or patient support may be configured for a support and/or positioning of the patient. For example, the patient may be positioned and/or supported with the patient table during the pre-interventional imaging and/or during the intervention.

Therein, the holding apparatus may be configured such that the patient may be positioned between a support area of the patient table and the contact area of the pressure plate.

Therein, a spacing between the pressure plate and the support area may be pre-determined by the holding apparatus. Therein, the spacing may be fixed and unchangeable. Alternatively, the spacing may be variable. For example, the spacing may be adaptable to the patient. For example, the spacing may be adaptable such that, via the pressure plate, a constant pressure is applied to the patient, regardless of whether the medical technology device or the force module is coupled to the pressure plate.

For example, in this manner, the force module may be integrated into the pressure plate. In other words, the force module may be realized via the holding apparatus.

Via an arrangement of the holding apparatus on the patient table, a self-calibrated system may be provided. In this case, "calibrated system" provides that, via the spacing of the pressure plate from the support area pre-determined by the holding apparatus, the interventional pressure is constant, regardless of whether the medical technology device or the force module is coupled to the pressure plate. The spacing between the pressure plate and the patient table and/or a support area of the patient table therein depends only upon the position of the pressure plate on the holding apparatus. The patient may be moved with the patient table, where the pressure plate positioned via the holding apparatus does not change its position. In this way, a displacement of the patient, for example, from the pre-interventional imaging to the intervention is possible. Therein, it may be provided that the pressure plate remains positioned unchanged relative to the patient during the displacement.

According to a further aspect of the present embodiments, the positioning apparatus and the force module are included by a robotic system. The robotic system is therein configured to regulate a force applied by the force module or the medical device on the pressure plate such that the force measured with the force sensor is constant.

Alternatively, the position of the pressure plate is regulated and/or adapted via the robotic system such that a sum of the forces acting upon the pressure plate remains constant. The total of the forces is therein made up from the geodetically vertically downwardly acting weight force of the force module or of the medical technology device and the geodetically vertically upwardly acting force that is generated by the contact of the pressure plate with the patient. The force generated by the patient is therein greater the greater the force that is applied by the pressure plate to the patient is. Therein, the force generated by the patient corresponds to the force that the pressure plate applies to the patient.

Therein, the force sensor indicates, for example, the force that the patient exerts on the pressure plate. In other words, the force sensor indicates the force that the pressure plate applies to the patient. Therein, the force applied by the medical technology device or the force module onto the pressure plate may be greater or smaller than the force on the patient.

Therein, the robotic system is, for example, configured such that the position of the pressure plate relative to the patient remains constant, regardless of whether the medical technology device is coupled to the pressure plate or not. The force applied to the pressure plate thus also remains constant, regardless of whether the medical technology device is coupled to the pressure plate or not.

The robotic system may regulate itself using a feedback message and/or a measurement value from the force sensor.

According to a further aspect of the present embodiments, the pressure applied by the force module and the pressure plate is regulated by the robotic system via a displacement of the pressure plate arranged on the holding apparatus with the positioning apparatus.

For example, the robotic system includes the holding apparatus for positioning the pressure plate. The pressure relates therein to the pressure applied to the patient. For example, the pressure relates to the pressure applied during the pre-interventional imaging. For example, this pressure may represent the interventional pressure. For example, the pressure may also relate to the pressure applied during the intervention (e.g., the interventional pressure).

For example, the robotic system with the holding apparatus may lower and/or displace the pressure plate in the direction of the positioning of the patient. For example, the pressure plate may be lowered and/or displaced at least for as long as the contact area of the pressure plate is in contact with and/or touches the patient. Alternatively, the pressure plate may be further lowered and/or displaced by the holding apparatus, and in this way, a pressure is generated on the patient with the pressure plate. In other words, the robotic system may exert a force with the holding apparatus on the pressure plate that, in turn, generates and/or applies a pressure to the patient. The force applied via the holding apparatus may therein be detected with the force sensor. The force applied by the force module therein corresponds to the force applied by the holding apparatus. In other words, the holding apparatus then includes the force module.

In some embodiments, the medical technology device may be coupled to the pressure plate without the pressure plate being displaced.

The force for generating the interventional pressure for the pre-interventional imaging may be generated mechanically by a "pressing" and/or "pressure" of the pressure plate with the holding apparatus onto the patient. Therein, the pressure plate is displaced by the holding apparatus for pressing. In this way, the pressure on the patient may be regulated flexibly and steplessly and independently of a weight force of the force module.

According to a further aspect of the present embodiments, the robotic system is configured, by positioning the force module and/or the medical technology device, to adapt the interventional pressure.

For example, the robotic system is configured to regulate the force applied by the force module and/or the medical technology device onto the pressure plate. If, for example, the medical technology device is coupled to the pressure plate, the weight force of the medical technology device acts geodetically vertically downwardly onto the pressure plate. In order to reduce the force acting on the pressure plate, the robotic system may lift the medical technology device and, in this way, relieve the pressure plate. The interventional pressure therein corresponds to the pressure that is brought about by the reduced weight force on the pressure plate.

Analogously, in some embodiments, the robotic system may lift the force module in order to relieve the pressure plate if the force module is coupled to the pressure plate.

For example, in this way, the robotic system may relieve the pressure plate such that the same force always acts upon, and/or is applied to, the pressure plate. In other words, in this way, the robotic system may regulate the force acting upon the pressure plate.

For example, using the force sensor, it may be tested whether the force on the pressure plate corresponds to the force that generates the interventional pressure. If this is not the case, the robotic system may relieve the pressure plate by more or less.

In order to relieve the pressure plate, the robotic system may grasp the force module and/or the medical technology device. For example, the robotic system may grasp the force module and/or the medical technology device with a robot arm. For this purpose, the robotic system includes at least one robot arm with a gripping apparatus. For example, the robotic system may then couple either the force module or the medical technology device to the pressure plate. The robot arm is configured to position the medical technology device and/or the force module. The robot arm is therein configured to position the medical technology device and/or the force module relative to the pressure plate.

Alternatively, the force module and/or the medical technology device may be arranged on the robotic system. For example, the force module and/or the medical technology device may each be arranged on a robot arm of the robotic system. For this purpose, the robotic system includes at least one or two robot arms. The medical technology device and/or the force module may be screw fastened to the relevant robot arm. For example, the robotic system may then couple either the force module or the medical technology device to the pressure plate. The relevant robot arm is configured to position the medical technology device and/or the force module. The relevant robot arm is configured to position the medical technology device and/or the force module relative to the pressure plate.

For example, the medical technology device may be grasped by a robot arm with a gripping apparatus included by the robotic system, and the force module may be fastened to a further robot arm included by the robotic system. Alternatively, the force module may be grasped by the robot arm with a gripping apparatus included by the robotic system, and the medical technology device may be fastened to a further robot arm included by the robotic system.

In an alternative embodiment, the force sensor is also configured to measure a force acting on at least one of the robot arms described above. For example, the force sensor therein measures the force that the patient exerts, as described above, on the pressure plate and/or the medical technology device. For example, then, during positioning of the medical technology device with the robotic system, the pressure plate may previously be removed from the patient. In other words, the pressure plate is not positioned at or on the patient when the medical technology device is positioned. Therein, the medical technology device is positioned (e.g., with a robot arm of the robotic system). For example, the medical technology device may therein be positioned such that the force generated by the patient on the pressure plate with the force module positioned corresponds to the force generated by the patient on the medical technology device.

The weight force of the force module and/or of the medical technology device acting upon the patient may be regulated with the robotic system. For this purpose, the robotic system may relieve the pressure plate and/or reduce the force acting upon the patient.

According to a further aspect of the present embodiments, the imaging system is a computed tomography system or a magnetic resonance tomography system or a C-arm system.

For the pre-interventional imaging, a computed tomography system or a magnetic resonance tomography system or a C-arm system is often used. The interventional pressure may be applied to the patient via the pressure control system, even during a capture of a medical image with a computed tomography system or a magnetic resonance tomography system or a C-arm system.

According to a further aspect of the present embodiments, the intervention is a histotripsy. Therein, the medical technology device is a histotripsy system.

Therein, the histotripsy system is configured as described above.

The histotripsy system cannot yet be positioned during the pre-interventional imaging, since the space requirement of the histotripsy system is too great. The influence of the histotripsy system on the patient may be simulated with the pressure control system.

The present embodiments further relate to a method for providing an interventional pressure to be applied to a defined area of a patient during a pre-interventional imaging process with an imaging system. Therein, the interventional pressure corresponds to an interventional pressure applied to the defined area of the patient during an intervention via a medical technology device. The method includes a method act of positioning a pressure plate relative to the patient with a positioning apparatus. Therein, a force module applies a force to the pressure plate. Therein, the force generates the interventional pressure upon the pressure plate. The method further includes a method act of a positioning of the patient in an imaging system for the pre-interventional imaging while the interventional pressure is applied to the patient via the pressure plate and the force module. The method further includes a method act of positioning the patient outside the imaging system. The method further includes a method act of removing the force module. The method further includes a method act of positioning the medical technology device relative to the patient such that the position of the medical technology device relative to the patient corresponds to the position of the pressure plate or the force module during the pre-interventional imaging.

The definitions, examples, and aspects according to the description relating to the pressure control system may be transferred similarly to the corresponding expressions and/or descriptions relating to the method.

In the method act of positioning the pressure plate, the pressure plate is positioned relative to the patient. Therein, the pressure plate is positioned, for example, on the intervention region of the patient. For example, the patient may therein be positioned lying on a patient table. For example, the pressure plate may be placed on the patient from above. Therein, the pressure plate lies with the contact area on the patient.

The force module may be arranged, for example, on the side of the pressure plate opposite to the contact area. The force module may be coupled (e.g., as described above) to the pressure plate. For example, the force module may be able to be releasably coupled to the pressure plate. Therein, the force module applies a force to the pressure plate. The force on the pressure plate therein acts upon the patient. The pressure may therein represent the interventional pressure.

In the method act of positioning the patient in an imaging system, the patient is positioned in the imaging system for the pre-interventional imaging. During the pre-interventional imaging, the medical image of the patient is captured. The medical image may subsequently serve for an image-based planning of the intervention. For the pre-interventional imaging, the patient may be positioned (e.g., on the patient table in the imaging system). Therein, the pressure plate and the force module applies the interventional pressure to the patient. In other words, the pressure plate and the force module apply the interventional pressure to the patient during the pre-interventional imaging.

In the method act of positioning the patient outside the imaging system, the patient may be moved, for example, out of the imaging system on the patient table. Alternatively, the patient may leave the imaging system independently.

In the method act of removing the force module, the force module is removed from the patient. For example, for this purpose, the force module may be decoupled from the pressure plate. Then, the force module may be removed while the pressure plate remains in position. Alternatively, the force module may be removed with the pressure plate.

If the force module is included by a holding apparatus or a robotic system, the removal of the force module may include a reduction of the pressure by the pressure plate. The reduction of the pressure may take place by a change in the position of the pressure plate using the holding apparatus or the robotic system.

In the method act of positioning the medical technology device, the medical device is positioned relative to the patient. Therein, the medical technology device is positioned such that a position of the medical technology device relative to the patient corresponds to the position of the pressure plate or the force module during the pre-interventional imaging.

For this purpose, the medical technology device may be positioned similarly to the force module such that the medical technology device applies a force to the pressure plate. For example, the medical technology device may be coupled to the pressure plate during the positioning of the medical technology device.

Alternatively, if the pressure plate has been removed with the force module, the medical technology device may be positioned similarly to the position of the pressure plate relative to the patient. For this purpose, the medical technology device may include an area that corresponds in shape and extent to the contact area of the pressure plate. For example, the area of the medical technology device and the contact area represent the defined area. The medical technology device may be positioned on the basis of and/or using a marking relative to the patient, so that a position of the medical technology device relates to the position of the pressure plate. For this purpose, the marking may be tattooed or painted and/or drawn onto the patient. Alternatively, the marking may be projected with a light source and/or an illumination device (e.g., a laser and/or a lamp) onto the patient. The marking may specify, for example, at least one position of a corner or an edge of the contact area of the pressure plate and/or the medical technology device on the patient. Alternatively, the marking may specify, for example, an outline of the pressure plate and/or the medical technology device on the patient.

In this way, a deformation of the organs and/or the soft tissue of the patient may be provided during the pre-interventional imaging similarly to the deformation during the intervention. In this way, the intervention may be planned based on the medical image captured during the pre-interventional imaging. The pressure plate and the force module may apply the interventional pressure to the patient also during the pre-interventional imaging.

According to an optional aspect of the present embodiments, the medical technology device may be positioned such that the deformation of the intervention region by the medical technology device corresponds to the deformation during the pre-interventional imaging. Therein, the positioning of the medical technology device may be based upon the medical image.

In other words, via the positioning of the medical technology device, a deformation of the intervention region may be brought about in a targeted manner. Therein, the deformation may be brought about such that it corresponds to a deformation mapped on the medical image.

A targeted deformation of the intervention region is possible based on the medical image.

According to one aspect of the present embodiments, the medical technology device is positioned in the act of positioning on the pressure plate.

For example, the medical technology device may be coupled to the pressure plate. For example, the medical technology device may be releasably coupled to the pressure plate, as described above.

In this way, the medical technology device is reliably positioned identically to the force module. In other words, the contact area with the patient to which the medical technology device applies a force, is the same as the contact area to which the force module applies a force during the pre-interventional imaging. In this way, it may be provided that the area that applies the interventional pressure to the patient during the pre-interventional imaging and during the intervention are the same.

According to a further aspect of the present embodiments, the method also includes a method act of removing the pressure plate.

Therein, the pressure plate is removed (e.g., after or simultaneously with the force module). For example, the pressure plate is removed before the positioning of the medical technology device. For example, the medical technology device may be positioned as described above based on the marking, similarly to the pressure plate. For example, in the method act of positioning the pressure plate, the pressure plate may then also have been positioned based on the marking.

By the removal of the pressure plate, a direct contact may be generated between the patient and the medical technology device. This may be advantageous, for example, dependent upon the medical technology device and the intervention. For example, a direct contact of the medical technology device with the patient for coupling ultrasonic waves into the patient may be advantageous. Alternatively, the direct contact of the medical technology device with the patient may be advantageous if, using the medical technology device, an invasive intervention is carried out and a direct access from the medical technology device to the patient is to be provided.

The present embodiments further relate to a system that is configured to carry out a method described above and its aspects. The system includes a pressure control system as described above and a medical technology device. The medical technology device therein includes a histotripsy system.

BRIEF DESCRIPTION OF THE DRAWINGS

The above-described properties, features and advantages of this invention are more clearly and distinctly described in the context of the following description making reference to the drawings. The drawings and descriptions are not intended to restrict the invention and embodiments of the invention in any way.

In the different drawings, the same components are provided with corresponding reference signs. The drawings are in general not to scale.

FIG. 9 shows an exemplary embodiment of a method for providing an interventional pressure to be applied to a patient during a pre-interventional imaging process with an imaging system.

DETAILED DESCRIPTION

Figure 1:
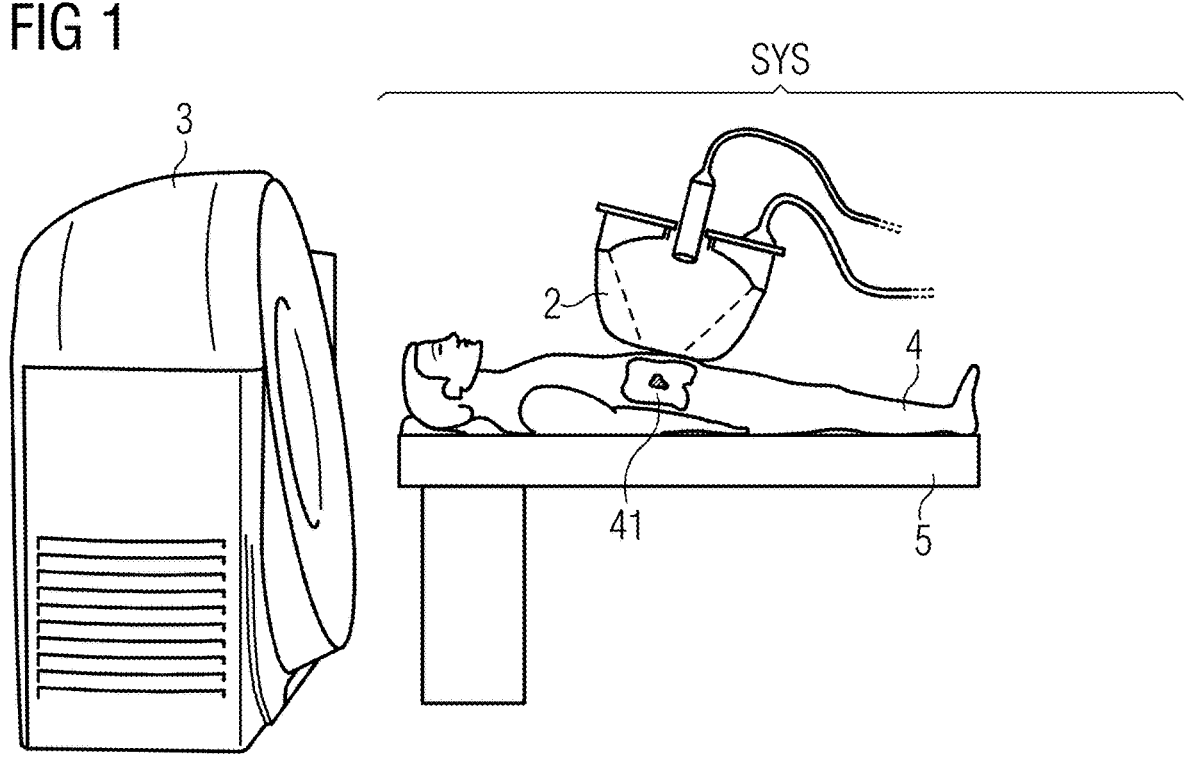
FIG. 1 shows a prior art arrangement.

FIG. 1 shows a prior art arrangement.

It is known, in advance of an intervention on a patient 4, to carry out a pre-interventional imaging with an imaging system 3. Therein, a medical image of at least one intervention region of the patient 4 is captured. The patient 4 is therein positioned (e.g., on a patient table 5).

The imaging system 3 may therein be a computed tomography (CT) system or a magnetic resonance tomography (MRT) system. Alternatively, the imaging system may therein be an X-ray system, a mammography system, a C-arm system, a positron emission tomography (PET) system, or a single photon emission computed tomography (SPECT) system.

Therein, the patient is a human 4. Alternatively, the patient 4 may be an animal or an object. The intervention region is therein (e.g., the region of the patient 4 in which the intervention is to be carried out).

The intervention is carried out with a medical technology device 2. The medical technology device 2 may be positioned, for example, as shown on the patient 4. Therein, the medical technology device 2 applies an interventional pressure to the patient 4. The medical technology device 2 therein lies on a defined area that covers the intervention region on the patient 4. The defined area is thus specified by the intervention region. For example, the defined area is specified by an embodiment of the medical technology device. Therein, at least one organ and/or soft tissue 41 of the patient 4 may be compressed and/or distorted.

The medical technology device 2 typically cannot be positioned on the patient 4 during the pre-interventional imaging, since typically the space requirement is too large for the imaging system 3 and/or the medical technology device 2 would lead to artifacts in the medical image.

Thus, the interventional pressure typically only acts on the intervention region and/or on the patient 4 during the intervention. During the pre-interventional imaging, the interventional pressure does not act on the intervention region and/or on the patient 4.

This has the result that the organ and/or the soft tissue 41 is not distorted in the medical image. Thus, an exact planning of the intervention based upon the medical image is not possible.

The medical technology device represented here is a histotripsy system. The intervention that is carried out with the histotripsy system is a histotripsy. The histotripsy system includes an ultrasonic imaging transducer, an ultrasonic treatment transducer, and a coupling medium. The coupling medium serves for coupling the ultrasonic waves into the body of the patient 4. The coupling medium may therein be a water bath. In order to improve further the coupling of the ultrasonic waves into the body of the patient 4, a pressure is typically applied to the patient with the histotripsy system.

Figure 2:
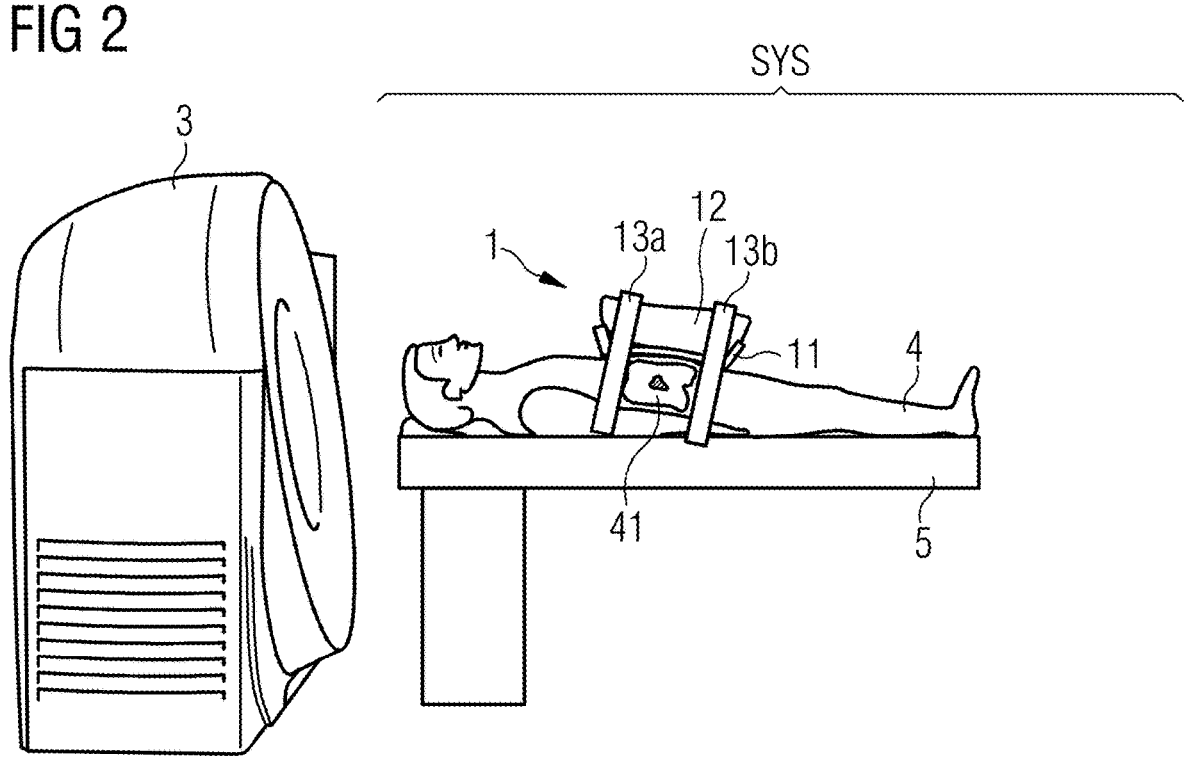
FIG. 2 shows a first exemplary embodiment of a pressure control system with a positioned force module.

FIG. 2 shows a first exemplary embodiment of a pressure control system 1 with a positioned force module 12.

The pressure control system 1 includes a pressure plate 11, a force module 12, and a positioning apparatus 13a, 13b.

The pressure plate 11 therein includes a contact area that is in contact with and/or lies on the patient 4. In some embodiments, the contact area of the pressure plate 11 corresponds in an extent and a shape to the area defined as described in relation to FIG. 1, with which a medical device (e.g., as described in relation to FIG. 1) lies on the patient 4.

Therein, the force module 12 applies a force to the pressure plate 11. In this exemplary embodiment, the force module 12 applies the force in the form of a weight force onto the pressure plate 11. Therein, the weight force of the force module 12 corresponds to the weight force of the medical technology device 2. In this way, the medical technology device 2 applies the same weight force to the same area as the force module 12 applies to the pressure plate 11. In this way, the interventional pressure described in relation to FIG. 1 is applied both by the medical technology device 2 to the patient and also by the force module 12 that applies a force to the pressure plate 11 (e.g., a weight force).

The positioning apparatus 13a, 13b is configured to position the pressure plate 11 and the force module 12 relative to the patient 4. For this purpose, in this exemplary embodiment, the pressure plate 11 and the force module 12 are fastened to the patient with belts. The positioning apparatus 13a, 13b includes two belts for this purpose.

In order to position the pressure plate 11 identically to the medical technology device 2 in FIG. 1, the pressure plate 11 and/or the medical technology device 2 may be positioned making use of a marking. For example, the pressure plate 11 and the force module 12 may therein be positioned with the positioning apparatus 13a, 13b. The marking may therein be a tattoo and/or a painted-on marking on the patient 4. Alternatively or additionally, the marking may be projected onto the patient 4 by an illumination device (e.g., by a laser). The marking may specify, for example, a position of an edge or a corner of the contact area of the pressure plate 11 and/or the corresponding area of the medical technology device 2 on the patient 4. Alternatively, the marking may mark the outline of the contact area of the pressure plate 11 and/or of the corresponding area of the medical technology device 2 on the patient 4.

The pressure plate 11 therein consists, in some embodiments, of a material that is compatible with the pre-interventional imaging. "Compatible" herein may be that the pressure plate 11 causes no or only slight artifacts in the medical image. Alternatively or additionally, if the pre-interventional imaging is based upon X-ray radiation, the pressure plate 11 should attenuate and/or absorb the X-ray radiation as little as possible. If the pre-interventional imaging includes a magnetic resonance tomography, the pressure plate should consist of a non-ferromagnetic material. Similarly, the force module 12 may consist of a material that is compatible with the pre-interventional imaging.

Figure 3:
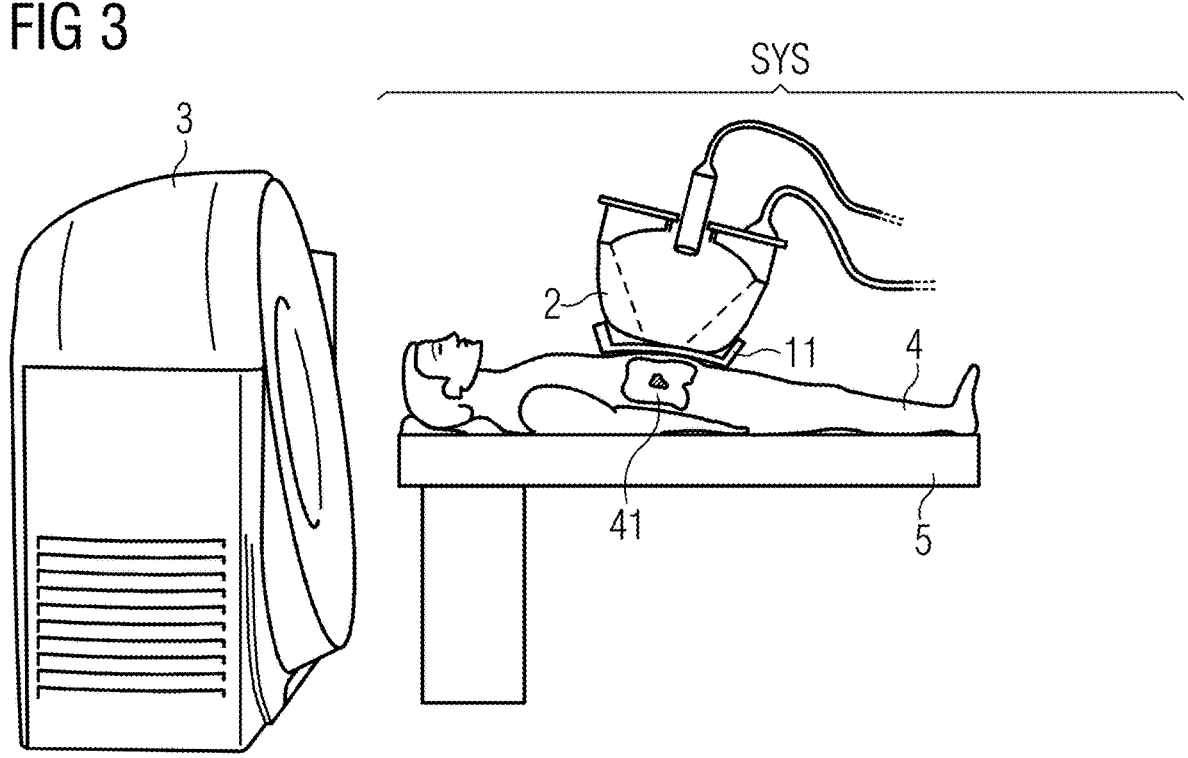
FIG. 3 shows an enhancement of the first exemplary embodiment of the pressure control system with a positioned medical technology device.

FIG. 3 shows an enhancement of the first exemplary embodiment of the pressure control system 1 with a positioned medical technology device 2.

The exemplary embodiment shows an enhancement of the first exemplary embodiment according to FIG. 2.

The medical technology device 2 is positioned on the pressure plate 11. For this purpose, the pressure plate 11 described in relation to FIG. 2 may be configured in a manner so as to be coupled to the medical technology device 2 or the force module 12. In other words, either the force module 12 or the medical technology device 2 may be coupled to the pressure plate 11. Therein, the force module 12 or the medical technology device 2 may be releasably coupled to the pressure plate 11. For example, the force module 12 and the medical technology device 2 may be releasably coupled or connected to the pressure plate 11 by a clip apparatus, a clamping apparatus, a tensioning apparatus, or a plug-in apparatus.

For example, no marking according to FIG. 2 is necessary to position the medical technology device 2 identically to the pressure plate 11. The pressure plate 11 may be positioned once relative to the patient 4. For the pre-interventional imaging, the force module 12 may then be coupled to the pressure plate 11. For the intervention, the force module 12 is replaced by the medical technology device 2 that is coupled to the pressure plate 11.

In this case, the medical technology device 2 includes no area that lies directly on the patient 4. Since both the medical technology device 2 and also the force module 12 lie on the patient 4 over the pressure plate 11 (e.g., over a contact area), it is provided that the force applied by the force module 12 and the medical technology device 2 act upon the same area (e.g., the area of the intervention region).

Figure 4:
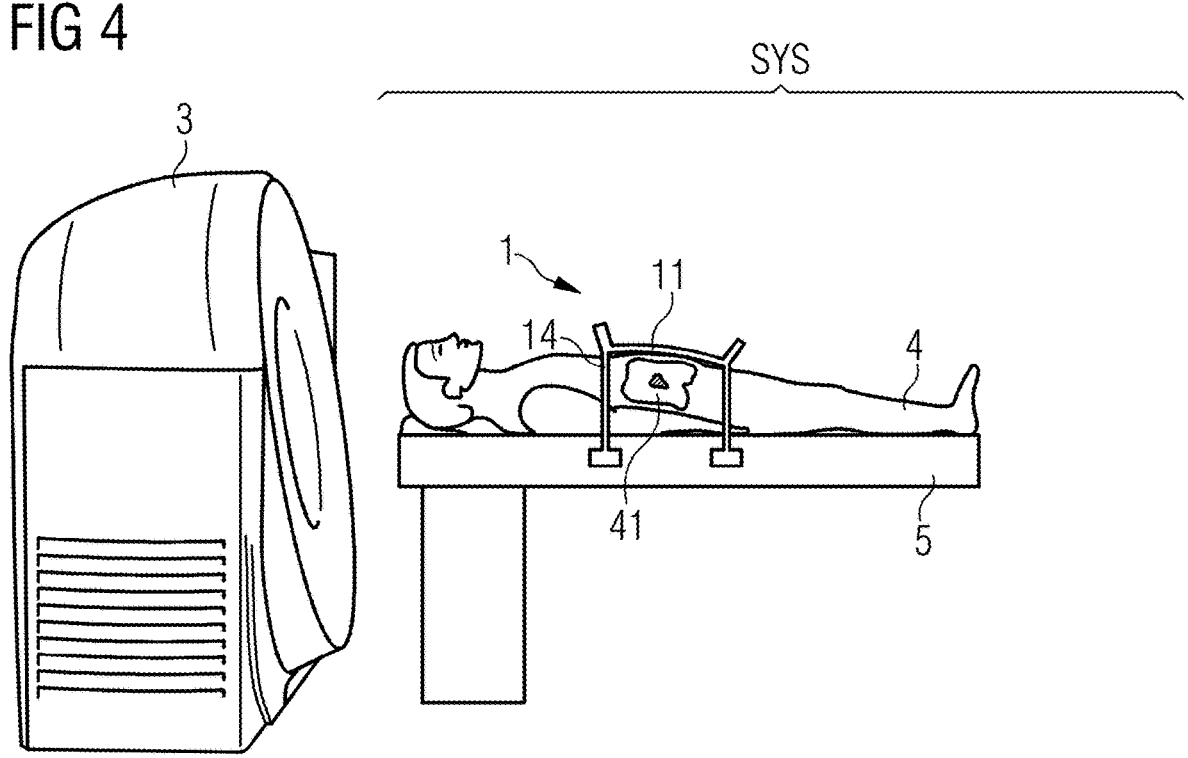
FIG. 4 shows a second exemplary embodiment of a pressure control system.

FIG. 4 shows a second exemplary embodiment of a pressure control system 1.

In this exemplary embodiment, the pressure control system 1 and, for example, the positioning apparatus include a holding apparatus 14. The pressure plate 11 is arranged on the holding apparatus 14. For example, therein, in some embodiments, the holding apparatus 14 may be arranged on a patient table 5 as shown. The patient 4 may become or be supported and/or positioned on a support area of the patient table 5. The patient 5 may therein be positioned between the pressure plate 11 and the patient table 5.

The holding apparatus 14 may specify a defined spacing between the support area of the patient table 5 and the pressure plate 11. For this, the holding apparatus 14 may be rigidly constructed.

For example, the defined spacing may be capable of adaptation to the patient 4. For example, the defined spacing may be adapted such that the pressure plate 11 lies on the patient 4.

For example, the force module 12 is included by the holding apparatus 14. The force on the pressure plate 11 in order to cause the interventional pressure may be applied by the holding apparatus 14. For example, this force may be caused by adjusting the defined spacing dependent upon the patient 4. Therein, by a "pressing" and/or "pushing" of the pressure plate 11 onto the patient 4 by the holding apparatus 14, the force for generating the interventional pressure may be applied to the patient. For this purpose, the spacing between the support area and the pressure plate 11 may be varied by the holding apparatus 14.

In alternative embodiments, the force module 12 may be arranged on the pressure plate 11 as described in relation to FIG. 2. For example, the force module may be able to be coupled to the pressure plate 11 as described in relation to FIG. 3.

Figure 5:
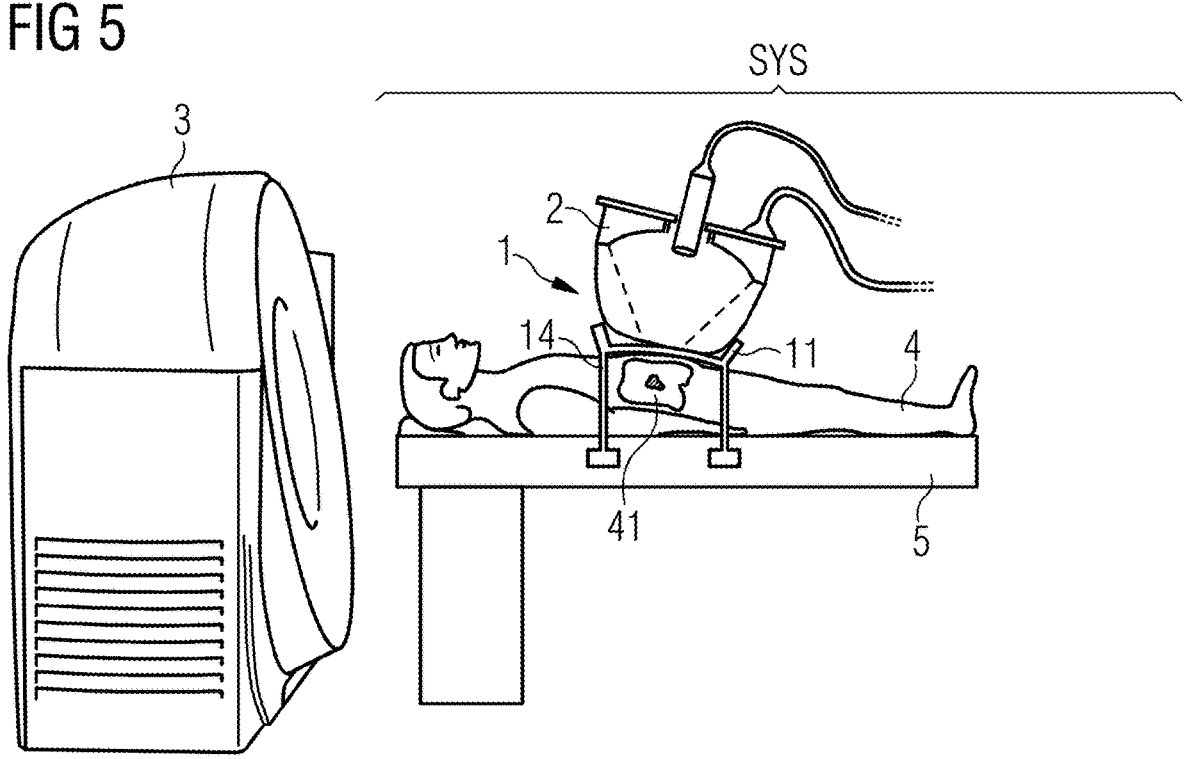
FIG. 5 shows the second exemplary embodiment of the pressure control system with a positioned medical technology device.

FIG. 5 shows the second exemplary embodiment of the pressure control system 1 with a positioned medical technology device 2.

The medical technology device 2 is positioned on the pressure plate 11. For example, the medical technology device 2 may therein be releasably coupled to the pressure plate 11 as described in relation to FIG. 3.

The pressure plate 11 is therein arranged, as described in relation to FIG. 4, with the holding apparatus 14 at a defined spacing from the support area of the patient table 5. Therein, the holding apparatus 14 is rigidly constructed. In other words, the holding apparatus 14 causes the spacing between the support area and the pressure plate 11 and/or between the patient 4 and the pressure plate 11 to remain constant, regardless of a weight force that acts upon the pressure plate 11.

The pressure control system 1 may therein include a force sensor. Using the force sensor, the force acting upon the pressure plate 11 may be captured and/or measured.

Figure 6:
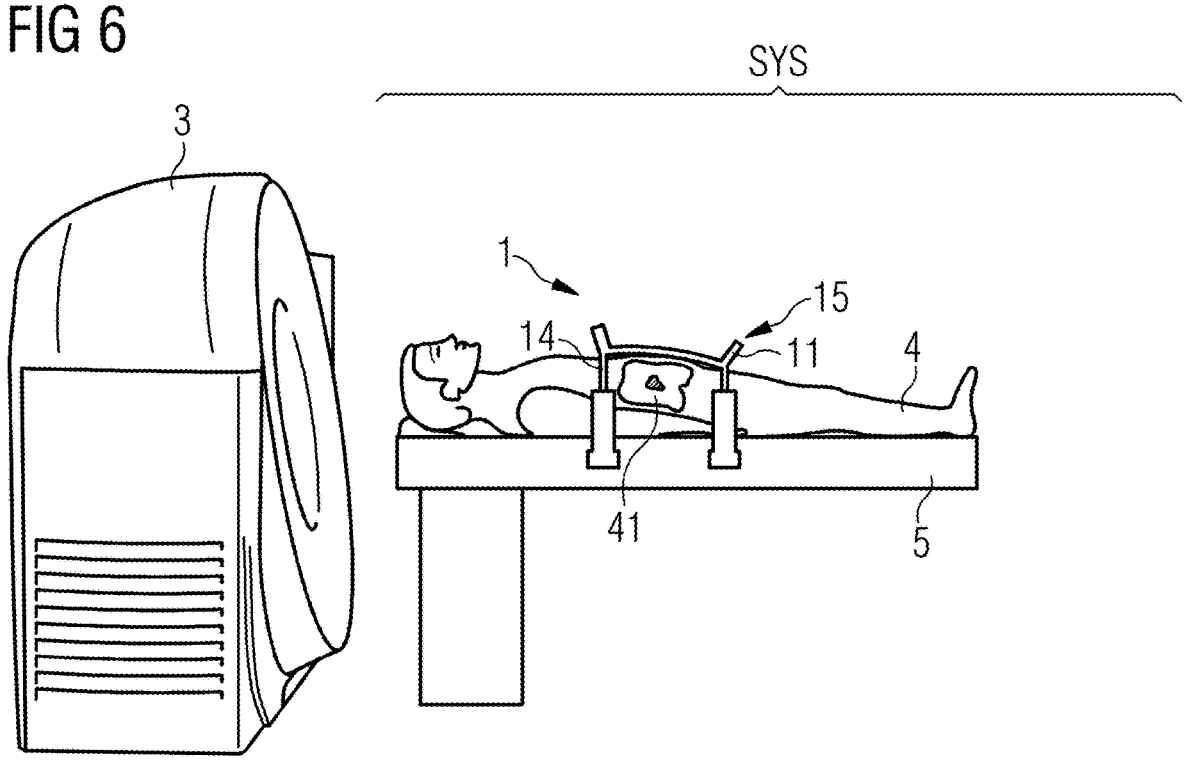
FIG. 6 shows a third exemplary embodiment of a pressure control system.

FIG. 6 shows a third exemplary embodiment of a pressure control system 1.

The pressure control system 1 is herein configured similarly to the second exemplary embodiment according to FIG. 4. Contrary to the second exemplary embodiment according to FIG. 4, the holding apparatus 14 herein includes a robotic system 15. The robotic system 15 may be configured, for example, to vary and/or adapt the defined spacing between the support area of the patient table 5 and the pressure plate 11 dependent upon the force action on the pressure plate 11.

For example, the pressure control system 1 may therein include a force sensor. The force sensor is configured, for example, to measure a force acting upon the pressure plate 11. For example, the robotic system 15 may be configured to regulate a force applied on the pressure plate 11 such that the force measured with the force sensor is constant. The force acting upon the pressure plate 11 may therein correspond to the force generated by the patient 4. This force corresponds to the force that the pressure plate 11 applies to the patient to generate the interventional pressure.

For example, for this purpose, the holding apparatus 14 may be flexibly configured. In other words, the pressure plate 11 may be movable by the holding apparatus 14.

Therein, the spacing between the support area of the patient table 5 and the pressure plate 11 is variable. The medical technology device 2 may be capable of being coupled to the pressure plate 11. If the medical technology device 2 is positioned on the pressure plate 11, the medical technology device 2 presses with at least its weight force on the pressure plate 11. The holding apparatus 14 may be configured such that this pressure is applied as the interventional pressure to the patient 4. During the pre-interventional imaging, the medical technology device 2 is removed and/or decoupled from the pressure plate 11. In order to generate a constant pressure (e.g., the interventional pressure) on the patient 4, the spacing may be reduced by the holding apparatus 14 between the support area and the pressure plate 11 such that the force sensor measures the same force as with the medical technology device 2 coupled. The force on the pressure plate 11 is therein applied by the holding apparatus 14. For example, the force is therein applied to the pressure plate 11 in that the spacing between the support area and the pressure plate 11 is reduced with the holding apparatus 14, and in this way, the pressure plate 11 is pressed onto the patient 4. For example, the holding apparatus 14 then includes the force module 12. The robotic system 15 may therein be configured to regulate the holding apparatus 14. For example, the regulation may be based upon a value measured by the force sensor.

Figure 7:
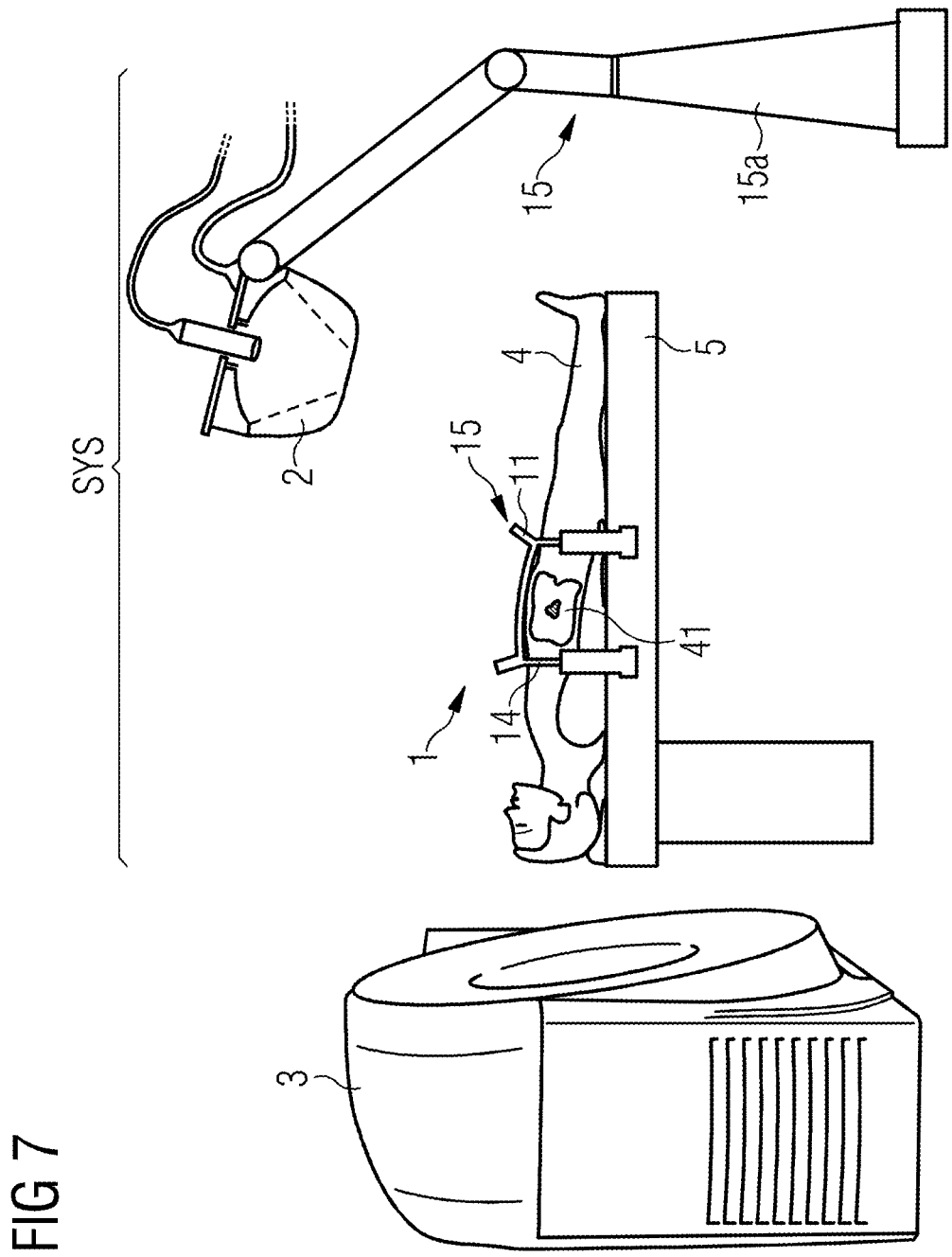
FIG. 7 shows a fourth exemplary embodiment of a pressure control system.

FIG. 7 shows a fourth exemplary embodiment of a pressure control system 1.

The holding apparatus 14 may therein be configured as per FIG. 5.

The robotic system 15 herein further includes a first robot arm 15*a* that is configured to position the medical technology device 2. For example, for positioning the medical technology device 2, the medical technology device 2 may be coupled to the pressure plate 11.

The medical technology device 2 is therein arranged on the first robot arm 15*a*. For this purpose, the medical technology device 2 may be, for example, screw fastened, welded, soldered, riveted, and/or cast onto the first robot arm 15*a*. Alternatively, the first robot arm 15*a* may be configured to grasp the medical technology device 2.

The first robot arm 15*a* is configured to place only a defined fraction of the weight of the medical technology device 2 on the pressure plate 11. In other words, the first robot arm 15*a* may at least partially relieve the pressure plate 11, so that the whole weight force of the medical technology device 2 does not act upon the pressure plate 11.

Therein, for example, the pressure plate 11 may be relieved such that the interventional pressure generated by the remaining weight force corresponds to a pressure generated by the holding apparatus 14 during the pre-interventional imaging without the medical technology device 2. The first robot arm 15*a* is therein controlled and/or regulated by the robotic system 15. The robotic system therein regulates the weight force applied by the medical technology device on the pressure plate 11 and/or the force applied to the pressure plate 11 by the holding apparatus by displacement of the defined spacing based on a value provided by the force sensor as described above. For example, the robotic system 15 regulates the interventional pressure acting upon the patient 4 at any time such that the force measured with the force sensor is constant.

Figure 8:
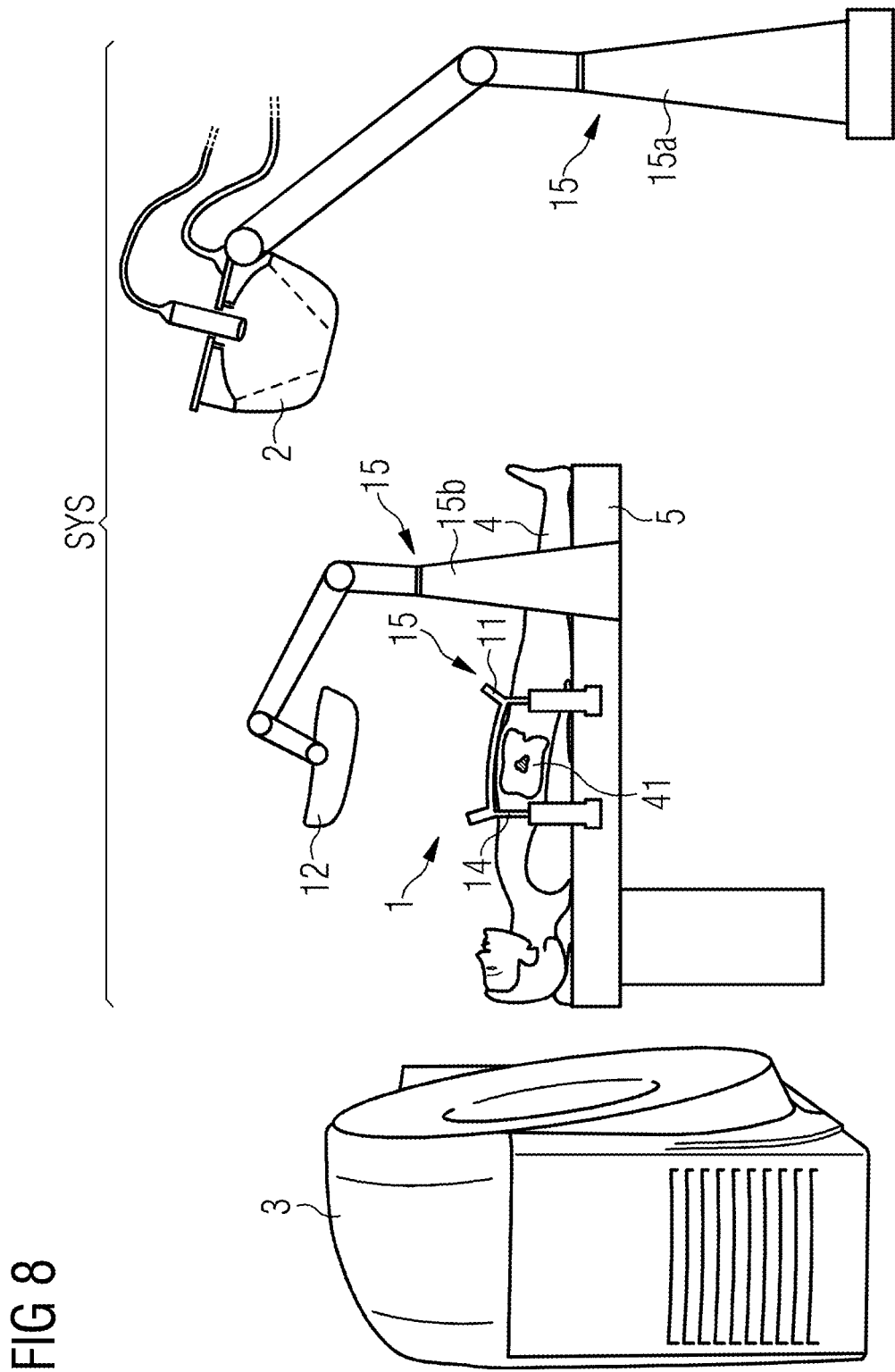
FIG. 8 shows a fifth exemplary embodiment of a pressure control system.

FIG. 8 shows a fifth exemplary embodiment of a pressure control system 1.

The fifth exemplary embodiment is based upon the fourth exemplary embodiment. However, therein, the interventional pressure is not regulated by the holding apparatus 14 during the pre-interventional imaging, but rather by a second robot arm 15*b*. The robotic system thus further includes the second robot arm 15*b*.

The second robot arm 15*b* is therein configured to position the force module 12. The force module 12 may therein be arranged on the second robot arm 15*b*. For example, the second force module 12 may be screw fastened, soldered, welded, riveted, and/or cast onto the second robot arm 15*b*. Alternatively, the second robot arm 15*b* may be configured to grasp the force module 12.

The second robot arm 15*b* is herein arranged, for example, on the patient table 5. Alternatively, the second robot arm 15*b* may also be arranged, for example, on a substrate beside the patient table 15*b* or in the imaging system 3.

The first robot arm 15*a* and the second robot arm 15*b* are therein controlled by the robotic system 15 such that either the medical technology device 2 or the force module 12 is coupled to the pressure plate 11. Therein, the first robot arm 15*a* and/or the second robot arm 15*b* relieve the pressure plate 11 such that a fraction of the weight force of the force module 12 acting on the pressure plate 11 corresponds to a fraction of the weight force of the medical technology device 2 acting upon the pressure plate 11. In other words, both when the force module 12 is coupled to the pressure plate 11 and also when the medical technology device 2 is coupled to the pressure plate 11, the same weight force acts on the pressure plate 11. Therefore, the interventional pressure that is applied by the pressure plate 11 and the corresponding fraction of the weight force of the force module 12 or the medical technology device 2 that is applied to the patient 4 is constant.

The robotic system 15 therein controls and/or regulates the first robot arm 15*a* and the second robot arm 15*b* based on a value measured by the force sensor as described above. For example, the robotic system 15 therein controls and/or regulates the first robot arm 15*a* and the second robot arm 15*b* such that the value measured by the force sensor is constant. Therein, the force sensor measures, for example, the force acting on the pressure plate 11 and/or the force acting on the first robot arm 15*a* and/or the second robot arm 15*a*.

In an alternative embodiment, the robotic system 15 may include a single robot arm that is configured to guide and/or position the force module 12 and the medical technology device 2. Therein, the robot arm may grasp either the force module 12 or the medical technology device 2. The positioning and relieving of the pressure plate 11 may therein be carried out similarly to the description with two robot arms 15*a*, 15*b*.

Different embodiments of a system SYS are represented in FIGS. 1 to 8. The system SYS therein includes an exemplary embodiment of a pressure control system 11 and a medical technology device 2. In the drawings in which the medical technology device 2 is not shown, the medical technology device 2 is merely not positioned on the pressure plate 11. The medical technology device 2 is nevertheless a constituent part of the system SYS. The same applies for the force module 12 that is also, in the non-positioned state, a constituent part of the pressure control system 1. The medical technology device 2 included by the system SYS is therein a histotripsy system.

FIG. 9 shows an exemplary embodiment of a method for providing an interventional pressure to be applied to a patient 4 during a pre-interventional imaging process with an imaging system 3.

The method may therein be carried out, for example, with one of the exemplary embodiments, described according to FIGS. 1 to 8, of a pressure control system 1 and a medical technology device 2.

In a method act of positioning S1 the pressure plate 11, the pressure plate 11 is positioned relative to the patient 4. Therein, the pressure plate 11 may be positioned with a positioning apparatus 13a, 13b. The pressure plate 11 is therein positioned, for example, on the intervention region of the patient 4. Therein, the pressure plate 11 may be positioned based on the marking described above. For example, the pressure plate 11 is positioned such that the pressure plate 11 corresponds to a position of the medical technology device 2 relative to the patient 4 during the intervention.

Meanwhile, the patient 4 may be positioned and/or supported on a patient table 5.

Therein, the force module 12 is arranged at or on the pressure plate 11. In an optional method act of a positioning of the force module 12, the force module 12 may be positioned on the pressure plate 11. The force module 12 may be capable of being releasably coupled to the pressure plate 11 as described above. Alternatively, the pressure plate 11 and the force module 12 may therein be firmly connected.

Therein, the force module 12 applies a force to the pressure plate 11. Therein, the force on the pressure plate 11 generates the interventional pressure on the patient 4. The force may therein be, for example, the weight force or at least a fraction of the weight force of the force module 12. Alternatively, the force module 12 may be realized, as per FIGS. 4 to 7, in the form of the holding apparatus 14.

The holding apparatus 14 may therein be included by the positioning apparatus. Alternatively, the positioning apparatus 13a, 13b may include, for example, at least one belt with which the pressure plate 11 and/or the force module 12 is positioned on the patient. The positioning apparatus may alternatively be included by a robotic system 15 described in relation to the preceding drawings.

In a method act of positioning S2 the patient 4 in an imaging system 3, the patient 4 is positioned for the pre-interventional imaging in the imaging system 3. The imaging system 3 may therein be configured as per FIG. 1. In the pre-interventional imaging, a medical image of at least the intervention region of the patient 4 may be captured.

During the pre-interventional imaging, the pressure plate 11 and the force module 12 may be positioned as described above.

In the method act of positioning S3 the patient 4 outside the imaging system 3, the patient 4 is again removed from the imaging system 3. For example, the patient 4 may be moved out of the imaging system 3 on the patient table 5. Alternatively, the patient 4 may leave the imaging system 3 independently.

In a method act of removing S4 at least the force module 12, the force module 12 is removed from the patient 4. Therein, the force module 12 may then be decoupled from the pressure plate 11. If the force module 12 is realized in the form of a holding apparatus 14, the removal S4 of the force module 12 may include a relieving of the interventional pressure of the holding apparatus 14 on the patient 4.

In an optional method act of removing S6 the pressure plate 11, the pressure plate 11 may be removed from the patient. This method act is carried out, for example, if the force module 12 is firmly connected to the pressure plate 11 or if the medical technology device 2 is not capable of being coupled to the pressure plate 11.

In a method act of positioning S5 the medical technology device 2, the medical technology device 2 is positioned relative to the patient 4. Therein, the medical technology device 2 is positioned such that the position of the medical technology device 2 relative to the patient 4 corresponds to the position of the pressure plate 11 or the force module 12 during the pre-operative imaging.

If the medical technology device 12 is capable of being releasably coupled to the pressure plate 11, the medical technology device 2 may be positioned at the site of the force module 12.

If the pressure plate 11 has been removed from the patient, the medical technology device 2 may be positioned relative to the patient 4 similarly to the pressure plate 11 (e.g., based on the marking). Therein, an area with which the medical technology device 2 lies on the patient 4 corresponds to the area and shape of the contact area of the pressure plate 11. The contact area is therein described above.

Where it has not yet explicitly been set out, although useful and in the spirit of the invention, individual exemplary embodiments, individual sub-aspects, or features thereof may be combined and/or exchanged with one another without departing from the scope of the present invention. Advantages of the invention described in relation to an exemplary embodiment also apply, where transferrable, to other exemplary embodiments without this being explicitly stated.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A pressure control system for providing an interventional pressure to be applied to a defined area of a patient during a pre-interventional imaging process with an imaging system, wherein, the interventional pressure corresponds to an interventional pressure applied via a medical technology device to the defined area of the patient during an intervention, the pressure control system comprising:
   a pressure plate;
   a force module; and
   a positioning apparatus,
   wherein the force module is configured to apply a force on the pressure plate,
   wherein the force on the pressure plate is operable to generate the interventional pressure,
   wherein the positioning apparatus is configured to position the pressure plate and the force module relative to the patient, and
   wherein the pressure plate comprises a coupling unit, and the force module or the medical technology device is releasably coupleable to the pressure plate via the coupling unit.

2. The pressure control system of claim 1, wherein the force applied by the force module on the pressure plate corresponds to a weight force applied by the medical technology device.

3. The pressure control system of claim 1, wherein the pressure plate comprises a contact area with the patient, and
wherein an extent and shape of the contact area of the pressure plate corresponds to an extent and shape of an area with which the medical technology device lies on the patient during the intervention.

4. The pressure control system of claim 3, wherein the pressure plate and the medical technology device are identically positionable relative to the patient with the positioning apparatus based on a marking.

5. The pressure control system of claim 1, wherein the pressure plate consists of a material that is compatible with the pre-interventional imaging.

6. The pressure control system of claim 1, further comprising:
a force sensor,
wherein the force sensor is configured to measure a force acting on the pressure plate.

7. The pressure control system of claim 1, wherein the positioning apparatus comprises a holding apparatus,
wherein the pressure plate is arranged on the holding apparatus, and
wherein the holding apparatus is configured to position the pressure plate relative to the patient.

8. The pressure control system of claim 7, wherein the holding apparatus is arranged on a patient table.

9. The pressure control system of claim 7, further comprising a force sensor configured to measure a force acting on the pressure plate,
wherein the positioning apparatus and the force module are included by a robotic system, and
wherein the robotic system is configured to regulate a force applied by the force module or the medical technology device to the pressure plate such that the force measured with the force sensor is constant.

10. The pressure control system of claim 9, wherein the pressure applied by the force module and the pressure plate is regulated by the robotic system via a displacement of the pressure plate arranged on the holding apparatus with the positioning apparatus.

11. The pressure control system of claim 9, wherein the robotic system is configured to position the force module, the medical technology device, or the force module and the medical technology device, such that the interventional pressure is adapted.

12. The pressure control system of claim 1, wherein the imaging system is a computed tomography system, a magnetic resonance tomography system, or a C-arm system.

13. The pressure control system of claim 1, wherein the intervention is a histotripsy, and
wherein the medical technology device is a histotripsy system.

14. A method for providing an interventional pressure to be applied to a defined area of a patient during a pre-interventional imaging process with an imaging system, wherein the interventional pressure corresponds to an interventional pressure applied to the defined area of the patient during an intervention via a medical technology device, the method comprising:
positioning a pressure plate relative to the patient with a positioning apparatus;
applying, by a force module, a force to the pressure plate, the force on the pressure plate generating the interventional pressure;
positioning the patient in an imaging system for the pre-interventional imaging while the interventional pressure is applied to the patient via the pressure plate and the force module;
positioning the patient outside the imaging system;
removing at least the force module; and
positioning the medical technology device relative to the patient such that the position of the medical technology device relative to the patient corresponds to the position of the pressure plate or the force module during the pre-interventional imaging,
wherein the medical technology device is positioned in the positioning of the medical technology device on the pressure plate.

15. A system comprising:
a pressure control system for providing an interventional pressure to be applied to a defined area of a patient during a pre-interventional imaging process with an imaging system, wherein the interventional pressure corresponds to an interventional pressure applied via a medical technology device to the defined area of the patient during an intervention, the pressure control system comprising:
a pressure plate;
a force module; and
a positioning apparatus, wherein the force module is configured to apply a force on the pressure plate, wherein the force on the pressure plate is operable to generate the interventional pressure, wherein the positioning apparatus is configured to position the pressure plate and the force module relative to the patient, and wherein the pressure plate comprises a coupling unit, and the force module or the medical technology device is releasably coupleable to the pressure plate via the coupling unit; and
the medical technology device, which comprises a histotripsy system.

* * * * *